(12) United States Patent
Hegazy et al.

(10) Patent No.: US 9,417,256 B2
(45) Date of Patent: Aug. 16, 2016

(54) SYSTEM, METHOD AND PROGRAM PRODUCT FOR AUTOMATICALLY MATCHING NEW MEMBERS OF A POPULATION WITH ANALOGOUS MEMBERS

(71) Applicants: Repsol, S.A., Madrid (ES); International Business Machines Corporation, Armonk, NY (US)

(72) Inventors: Mohamed Ahmed Hegazy, Heliopolis Cairo (EG); Sonia Mariette Embid Droz, Madrid (ES); Hilario Martin Rodriguez, Madrid (ES); Bruno Da Costa Flach, Copacabana (BR); Davi Michel Valladao, Sao Paulo (BR); Bianca Zadrozny, Rio de Janeiro (BR)

(73) Assignees: REPSOL, S. A., Madrid (ES); International Business Machines Corporation, Armonk, NY (US)

( * ) Notice: Subject to any disclaimer, the term of this patent is extended or adjusted under 35 U.S.C. 154(b) by 745 days.

(21) Appl. No.: 13/711,616

(22) Filed: Dec. 12, 2012

(65) Prior Publication Data
US 2014/0163901 A1    Jun. 12, 2014

(51) Int. Cl.
  *G01N 31/00*    (2006.01)
  *G01V 1/40*    (2006.01)
  (Continued)

(52) U.S. Cl.
  CPC .............. *G01N 37/00* (2013.01); *G01V 99/005* (2013.01); *G01V 2210/624* (2013.01); *G01V 2210/665* (2013.01)

(58) Field of Classification Search
  CPC ........... G01V 1/30; G01V 1/28; G01V 11/00; G01V 99/00; E21B 43/00; G01N 37/00
  USPC .............. 702/22, 6, 13, 11, 9, 34; 706/52, 46; 340/610
  See application file for complete search history.

(56) References Cited

U.S. PATENT DOCUMENTS 6,549,879 B1 *   4/2003   Cullick et al. .................. 703/10
7,519,476 B1 *   4/2009   Tnacheri et al. ................ 702/11
(Continued)

OTHER PUBLICATIONS

Hosein Hashemi; Logical considerations in applying pattern recognition techniques on seismic data: Precise ruling, realistic solutions; Apr. 2010; Institute of Geophysics, University of Tehran, Tehran, Iran; CSEG Recorder pp. 47-49.*

(Continued)

*Primary Examiner* — Gregory J Toatley
*Assistant Examiner* — Eman Alkafawi
(74) *Attorney, Agent, or Firm* — Law Office of Charles W. Peterson, Jr.; Louis J. Percello, Esq.

(57) ABSTRACT

A population comparison system, method and a computer program product therefor. A stored list of population members, e.g., hydrocarbon reservoirs, characteristics and analogous members is partitioned into lists for each member. A weighting system automatically uses the partitions to determine a weight set (w*) for population member characteristic and a similarity function. The weighting system may include an objective model that iteratively, blindly identifies analogous members for each population member until the identified analogous members match the listed analogous members. An analogous member selector uses the weights set (w*) and similarity function to automatically select analogous listed members for each new population member.

20 Claims, 4 Drawing Sheets

(51) Int. Cl.
*G01N 37/00* (2006.01)
*G01V 99/00* (2009.01)

(56) References Cited

U.S. PATENT DOCUMENTS

| | | | |
|---|---|---|---|
| 8,145,427 B1* | 3/2012 | Saleri et al. | 702/6 |
| 2004/0153299 A1* | 8/2004 | Colvin et al. | 703/10 |
| 2007/0050154 A1* | 3/2007 | Albahri | 702/22 |
| 2008/0319674 A1* | 12/2008 | Dai et al. | 702/6 |
| 2009/0276156 A1* | 11/2009 | Kragas et al. | 702/6 |
| 2009/0276157 A1* | 11/2009 | Wilkinson et al. | 702/8 |
| 2011/0118983 A1 | 5/2011 | Rowan | |
| 2011/0191029 A1* | 8/2011 | Jalali et al. | 702/6 |
| 2013/0317798 A1* | 11/2013 | Cheng et al. | 703/10 |

OTHER PUBLICATIONS

J.E. Hodgin et al., "The Selection, Application, and Misapplication of Reservoir Analogs for the Estimation of Petroleum Reserves" SPE 102505, 2006.

Vikas Bhushan et al., "A Novel Approach to Identify Reservoir Analogues," SPE 78338, Shell International Exploration and Production, 2002.

Amir Navot et al., "Nearest neighbor based feature selection for regression and its application to neural activity," Advances in Neural Information Processing Systems 18, 2006.

Hamarat et al., "A genetic algorithm based feature weighting methodology" International Conference on Computers and Industrial Engineering, Fac. of Technol., Policy & Manage., Delft Univ. of Technol., Delft, Netherlands, 2010.

* cited by examiner

1260 → $$\min \sum_{i \in I} \left(v_i - \theta_i^{\eta}\right)^2$$

SUBJECT TO:

1262 → $$v_i = \frac{1}{K} \sum_{j \in I\{i\}} \theta_j^{\eta} \cdot y_{ij} \qquad \forall i \in I$$

1264 → $$d_{ij} = \sum_{p \in P_{\eta}} w_p \cdot \delta_{ij}^p \qquad \forall i \in I, j \in I$$

1266 → $$d_{ij} \leq t_i + (1 - y_{ij}) \qquad \forall i \in I, j \in I$$

1268 → $$d_{ij} \geq t_i + y_{ij}$$

1270 → $$\sum_{p \in P_{\eta}} w_p = 1$$

1272 → $$\sum_{p \in P_{\eta}} y_{ij} = K \qquad \forall i \in I$$

Fig. 2B

SYSTEM, METHOD AND PROGRAM PRODUCT FOR AUTOMATICALLY MATCHING NEW MEMBERS OF A POPULATION WITH ANALOGOUS MEMBERS

BACKGROUND OF THE INVENTION

1. Field of the Invention

The present invention is related to valuating hydrocarbon reservoirs and more particularly to automatically selecting known analogous reservoirs for valuating newly identified hydrocarbon reservoirs.

2. Background Description

Each new hydrocarbon reservoir has an inherent total value that is based on unknown properties. In particular, the inherent value depends on the total amount of material that is ultimately recoverable from the reservoir (production potential) and the cost of recovering the material or capture difficulty. Until the material is actually recovered, those unknown properties remain unknown and the inherent value can only be estimated. Previously to estimate value, one or more experts first identified and selected existing reservoirs with certain similar aspects to the new reservoir, known as "analogous reservoirs." The expert(s) used the selected analogous reservoirs to estimate the value of the new reservoir. A misvaluation could lead to wasted resources, e.g., from passing on an undervalued reservoir to exploit an overvalued reservoir. So, to minimize errors, the trend has been to less reliance on subjective, expert judgment for subjectively selecting analogous reservoirs, and in turn, towards more objective selection approaches. For example, similarity functions have been used in valuing new hydrocarbon reservoirs.

Similarity functions have found many uses in the art today for comparing members of a collection of objects, or population, and selecting those objects that, although they not identical, are recognizably similar. A typical state of the art approach to determining similarity function parameters applies expert knowledge and/or local search methods, such as gradient descent and genetic algorithms. Generally, a common problem with these approaches is continued reliance on subjective judgment without necessarily arriving at the most similar matches.

A typical state of the art approach uses available reservoir information collected in a reservoir database and a similarity function to automate identifying and selecting analogous reservoirs. However, an expert (or experts) still chooses exact properties and weights used in the similarity function to compare any known properties of a target (new) reservoir with the properties of known reservoirs. Examples of manually specified (e.g., by experts specifying weights and/or properties) similarity functions selecting analogous reservoirs for estimating value are provided, for example, by published U.S. Patent Application No. 2011/0118983, "System and Method for Reservoir Analysis Background" to Rowan; and by Bhushan et al., "A Novel Approach to Identify Reservoir Analogues," Shell International Exploration and Production, 2002.

Hopefully, the expert chooses the best properties and weights to identify reservoirs with properties most similar to the target reservoir as analogous. Although this has automated identifying the final selection, it is still somewhat subjective because experts still choose the properties and weights. Consequently, selecting the best properties and weights is still subjective and makes selecting analogous reservoirs a difficult and error-prone task.

Thus, there is a need for improved application of similarity functions to comparing one object with other analogous objects from a population of similar objects; and, more particularly for automatically weighting similarity functions for selecting existing hydrocarbon reservoirs as analogous for valuating new reservoirs.

SUMMARY OF THE INVENTION

A feature of the invention is automatic selection of a set of weights and a similarity function for pairing a new population member with existing population members;

Another feature of the invention is automatically weighting reservoir characteristics for selecting analogous reservoirs for newly discovered reservoirs;

Yet another feature of the invention is automatic selection of an optimal set of weights for automatically weighting reservoir characteristics used for each newly discovered reservoir for selecting an optimum subset of known reservoirs as analogous reservoirs for valuating or appraising each newly discovered reservoir.

The present invention relates to a population comparison system, method and a computer program product therefor. A stored list of population members, e.g., hydrocarbon reservoirs, characteristics and analogous members is partitioned into lists for each member. A weighting system automatically uses the partitions to determine a weight set (w*) for population member characteristic and a similarity function. The weighting system may include an objective model that iteratively, blindly identifies analogous members for each population member until the identified analogous members match the listed analogous members. An analogous member selector uses the weights set (w*) and similarity function to automatically select analogous listed members for each new population member.

One embodiment is a population comparison method comprising: listing members of a population, characteristics for each population member and one or more analogous population members; weighting and comparing characteristics for each member against characteristics for each other member to identify members with the closest weighted characteristics; determining whether the identified members match listed analogous population members for said each member; returning to weighting and comparing characteristics until all identified members match listed analogous population members; and when all match providing a current set of weights (w*) and a similarity function for analogous members; receiving new population member descriptions including characteristics for each respective new population member; and selecting a subset of listed population members as analogous members for each new population member responsive to said current set of weights (w*) and said similarity function.

In this embodiment, weighting and comparing comprises partitioning said population (I) into one partition for each member (i, where i∈I), each partition includes two smaller populations or sub-groups. One sub-group includes the respective member and the other sub-group including all other members remaining after excluding the respective member. Population members are reservoirs with properties (p∈P), each property has a known value ($\theta_i^p$), and weighting and comparing comprises comparing said known value for a target property ($\eta$) against a property value estimate ($v_i \in R$: individual i∈I estimate of property $\eta \in P$) for said target property to arrive at property weights ($w_p \in [1,0]$). Comparing comprises applying an objective model minimizing the comparison difference, said objective model having the form: min $\Sigma_{i \in I}(v_i - \theta_i^\eta)^2$. The population comparison method may further comprise inputting to said objective model: $\theta_i^P \epsilon[1,0]$: (known) value of property p∈P of individual i∈I; and $\delta_{ij}^P \epsilon[1,0]$: distance along property p∈P between reservoirs i∈I and j∈I; and wherein reservoirs are separated by a distance, $d_{ij} \epsilon R$:i∈I and j∈I; and each reservoir has K neighboring reservoirs within a neighborhood threshold, $t_t \epsilon R$:i∈I. Further said objective model is subject to property estimate constraints, neighboring distance constraints, weight constraints, and neighboring member constraints; wherein property estimate constraints have the form $$v_i = \frac{1}{K} \sum_{j \in \Lambda\{i\}} \theta_j^\eta \cdot y_{ij};$$

neighboring distance constraints have the form $d_{ij} = \sum_{p \in P_n} w_p \cdot \delta_{ij}^P$, $d_{ij} \leq t_t + (1-y_{ij})$ and $d_{ij} \geq t_t + y_{ij}$; weight constraints have the form $\tau_{p \in P_n} w_p = 1$; and neighboring member constraints have the form $\sum_{j \in \Lambda\{i\}}^n y_{ij} = K$; where ∀i∈I and ∀j∈I. The subset may be selected by applying determined said weights (w*) to new population member characteristics; automatically selecting listed members satisfying a threshold as members of said subset; and determining a value for the new population member from said subset. The threshold may be a preselected number, said subset being said preselected number of listed members with weighted properties closest to said the new population member.

Another embodiment is a reservoir valuation method comprising: storing a reservoir database of known reservoirs, characteristics for each known reservoir and analogous said known reservoirs for said each known reservoir; automatically determining weights (w*) for known reservoir characteristics and a similarity function, comprising: weighting characteristics for said each known reservoir, comparing said each known reservoir against every other reservoir to identify the reservoirs with closest weighted characteristics, determining whether the identified reservoirs match listed said analogous known reservoirs for said each known reservoir, returning to weighting characteristics until all identified reservoirs match listed said analogous known reservoirs, and when all match providing a current set of weights (w*) and a similarity function for analogous members; receiving new reservoir descriptions including characteristics for each respective said new reservoirs; applying determined said weights (w*) to said new reservoir characteristics; automatically selecting a subset of known reservoirs satisfying a threshold; and determining a value for the said new reservoir from said subset.

In this embodiment, automatically determining weights further comprises partitioning said known reservoirs (I) into a plurality of partitions, one partition for each known reservoir (i, where i∈I), each partition includes two smaller reservoir populations or sub-groups. One reservoir sub-group includes the respective known reservoir (i) and the other reservoir sub-group including all other known reservoirs remaining after excluding the respective known reservoir. Reservoirs may be hydrocarbon reservoirs with properties (p∈P), each property has a known value ($\theta_i^P$), and comparing said known reservoirs comprises applying an objective model, said objective model comparing said known value for a target property (i) against a property value estimate ($v_i \epsilon R$: individual i∈I estimate of property η∈P) for said target property to arrive at property weights ($w_p \epsilon[1,0]$). Applying said objective model minimizes the comparison difference and has the form: min $\sum_{i \in I}(v_i - \theta_i^n)^2$; and wherein, inputs to said objective model include: $\eta_i^P \epsilon[1,0]$: (known) value of property p∈P of individual i∈I; and $\delta_{ij}^P \epsilon[1,0]$: distance along property p∈P between reservoirs i∈I and j∈I. The hydrocarbon reservoirs are separated by a distance, $d_{ij} \epsilon R$:i∈I and j∈I; each said hydrocarbon reservoir has K neighboring reservoirs within a neighborhood threshold, $t_t \epsilon R$: i∈I; and said objective model optimizes subject to property estimate constraints, neighboring distance constraints, weight constraints, and neighboring member constraints. Property estimate constraints have the form $$v_i = \frac{1}{K} \sum_{j \in \Lambda\{i\}} \theta_j^\eta \cdot y_{ij};$$

neighboring distance constraints have the form $d_{ij} = \sum_{p \in P_n} w_p \cdot \delta_{ij}^P$, $d_{ij} \leq t_t + (1-y_{ij})$ and $d_{ij} \geq t_t + y_{ij}$; weight constraints have the form $\sum_{p \in P_n} w_p = 1$; neighboring member constraints have the form $\sum_{j \in \Lambda\{i\}} y_{ij} = K$; where ∀i∈I and ∀j∈I; and said threshold is a preselected number, said member selection unit selecting said preselected number of known reservoirs with weighted properties closest to said the new reservoir.

Another embodiment is a computer program product for comparing members of a population, said computer program product comprising a computer usable medium having computer readable program code stored thereon, said computer readable program code causing a computer executing said code to: weight characteristics or properties for each member of a population, and compare each member against for every other member to identify members with the closest weighted characteristics, said list including characteristics for each population member and one or more analogous population members; determine whether the identified members match listed analogous population members for said each member; return to weighting and comparing characteristics until all identified members match listed analogous population members; and when all match provide a current set of weights (w*) and a similarity function for analogous members; receive new population member descriptions including characteristics for each respective new population member; and select a subset of listed population members as analogous members for each new population member responsive to said current set of weights (w*) and said similarity function.

Yet another embodiment is a computer program product for valuating reservoirs, said computer program product comprising a computer usable medium having computer readable program code stored thereon, said computer readable program code causing a computer executing said code to: automatically determine weights (w*) for known reservoir characteristics and a similarity function from data stored in a reservoir database, said reservoir database listing known reservoirs, characteristics for each known reservoir and analogous said known reservoirs for said each known reservoir, automatically determining weights (w*) comprising: weighting characteristics for said each known reservoir, comparing said each known reservoir against every other reservoir to identify the reservoirs with closest weighted characteristics, determining whether the identified reservoirs match listed said analogous known reservoirs for said each known reservoir, returning to weighting characteristics until all identified reservoirs match listed said analogous known reservoirs, and when all match providing a current set of weights (w*) and a similarity function for analogous members; receive new reservoir descriptions including characteristics for each respective said new reservoirs; apply determined said weights (w*) to said new reservoir characteristics; automatically select a subset of known reservoirs satisfying a threshold; and determine a value for the said new reservoir from said subset.

BRIEF DESCRIPTION OF THE DRAWINGS

The foregoing and other objects, aspects and advantages will be better understood from the following detailed description of a preferred embodiment of the invention with reference to the drawings, in which:

FIGS. 2A-B show an example of a property weighting system for automatically selecting properties and weights for application in an optimal similarity function;

DESCRIPTION OF PREFERRED EMBODIMENTS

Figure 1:
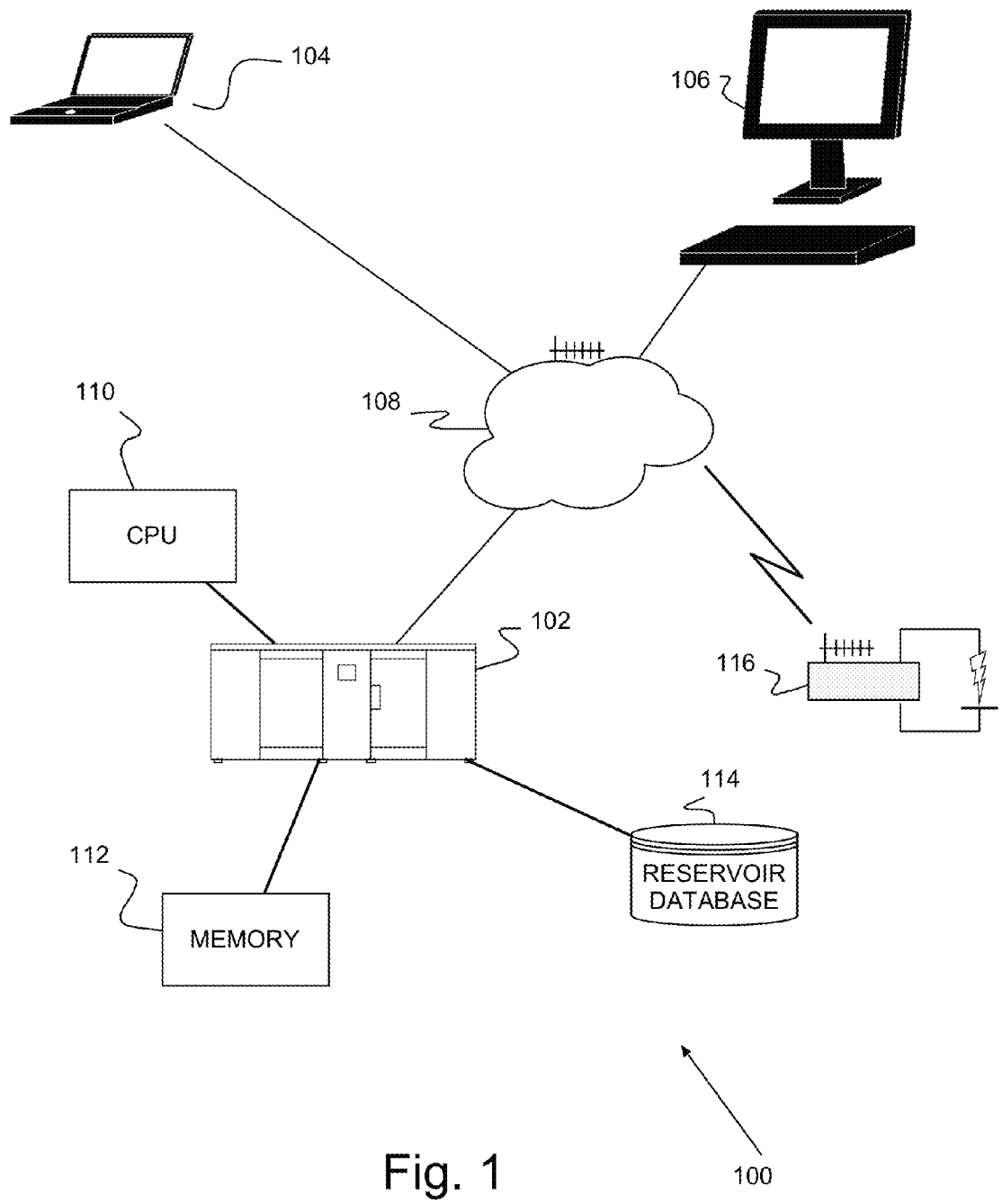
FIG. 1 shows an example of a preferred appraisal system for automatically pairing new population members (e.g., newly discovered hydrocarbon reservoirs) with existing population members according to a preferred embodiment of the present invention.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Turning now to the drawings and more particularly, FIG. 1 shows an example of an appraisal system 100 determining a valuation for new population members (e.g., newly discovered hydrocarbon reservoirs), based on automatic pairing with cataloged and characterized existing population members according to a preferred embodiment of the present invention. The appraisal system 100 includes computers 102, 104, 106 (3 in this example) coupled, wired or wirelessly to, and communicate with each other over, network 108, e.g., a local area network (LAN), the Internet, an intranet or a combination thereof. Typically, the computers 102, 104, 106 include one or more processors, e.g., central processing unit (CPU) 110, memory 112 and local storage 114 with a catalog listing known or existing population members, member characteristics and previously identified analogous members, e.g., a reservoirs database.

In this example, the preferred system 100 first automatically determines a set of weights (w*) for characteristics or properties for all existing population members for application in a similarity function. Preferably, the system 100 finds the set of weights and similarity function that result in the minimum valuation error for each population member based on comparing the actual value with an estimated valuation derived from all of the other population members and minimizing the differences between actual and estimate. Then, as new hydrocarbon reservoirs discovered and characterized, the preferred system 100 applies the weighted similarity function to newly discovered hydrocarbon reservoirs to identify analogous existing reservoirs. The system uses the identified analogous reservoirs to estimate the value of each newly discovered reservoir. New reservoir data may be received directly from remotely connected sensors 116, or automatically or manually entered into one or more of the networked computers 102, 104, 106.

Preferably, the reservoir database in storage 114 includes properties of a population of existing reservoirs. These properties may include, for example, geological aspects, petrophysical parameters, reservoir spatial or volumetric physical properties, and development scheme to extract the optimum weights. Geological aspects can include, for example, geological age, lithology, depositional environments and the diagenetic and structural history. Petro-physical parameters can include, for example, gross thickness, net-to-gross ratio, pay thickness, porosity, hydrocarbon saturations, and permeability. Reservoir spatial or volumetric physical properties can include, for example, depth, pressure, temperature, original fluid content, oil gravity, relative permeability, residual saturations and drive mechanisms. Development scheme can include, for example, well spacing, completion and stimulation, artificial lift, fluid injection, and injection volumes.

Initially, the preferred system 100 applies an optimization model to existing population members, or reservoirs, listed in the reservoir database in storage 114, automatically selecting weights and a similarity function. In particular, each listed member also has a subset of other listed members that are previously identified as analogous, e.g., analogous reservoirs. The optimization model iteratively, blindly identifies analogous reservoirs for each member and, in each iteration, compares the results against the known subset for each. By minimizing the difference, or error, in comparison results, the optimization model selects an optimum set of weights and similarity function for application to new, previously unknown members (reservoirs). Thereafter, as a new reservoir is discovered, the system 100 uses the selected weights and similarity function to select analogous reservoirs for estimating value.

Figure 2A:
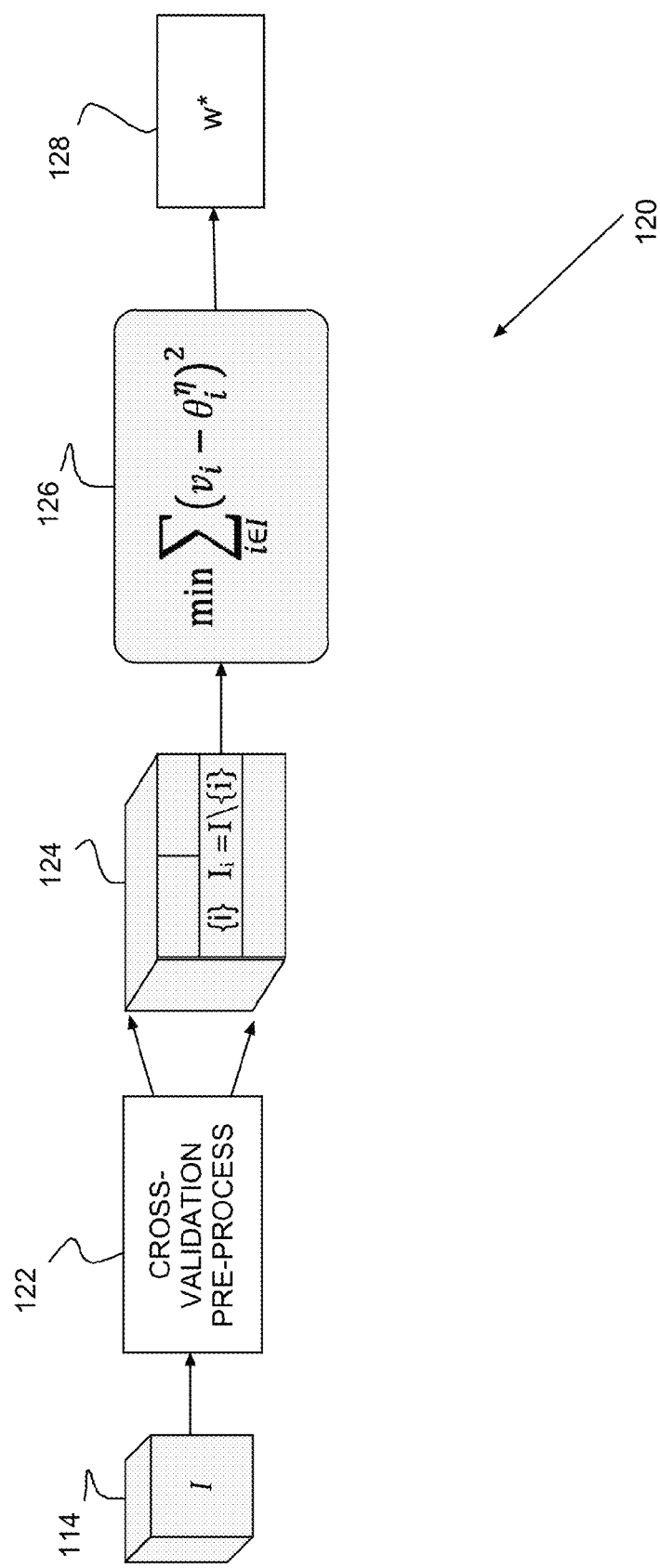

FIGS. 2A-B show an example of a property weighting system 120 for automatically selecting a set of property weights for weighting similarity function factors for identifying analogous reservoirs according to a preferred embodiment of the present invention. A cross-validation pre-processor 122 partitions the reservoir database (e.g., from storage 114 of FIG. 1) to create partitions 124, an individual partition for each reservoir. Then, applying an automatic weighting unit 126 to the individual partitions 124, the weighting unit 126 generates an optimal set of weights (w*) 128 for the population (I) of existing reservoirs (i, where i∈I) that best describe the similarity function for that population (I). In this example, the automatic weighting unit 126 applies an optimization model 1260, subject to constraints 1262-1272, to arrive at an optimal set of weights (w*) 128.

First, the cross-validation pre-processor 122 segments or partitions the entire reservoir population (I) in database 114, identifying one partition for each reservoir (R) with each partition including two smaller reservoir populations or sub-groups. One reservoir sub-group includes the respective reservoir (i, where i∈I) in a unitary validation dataset ({i}); and, the other reservoir sub-group or set includes all other reservoirs ($I_i = I \setminus \{i\}$), for a leave-one-out cross-validation (LOOCV). Details or properties ($p_i$) for each reservoir belong to a set of reservoir properties (P). For each individual reservoir (i∈I), each property (p∈P) has a known value ($\theta_i^p \in [1,0]$). The preferred property weighting system 120 selected a target property (η), and uses the remaining reservoir properties as a set ($P_\eta = P \setminus \{\eta\}$) to predict the target property (η).

Two reservoirs (i and j) have a 2-norm univariate distances ($\delta_{ij}^p$) between them, where $\delta_{ij}^p \in [1,0]$: distance along property p∈P between reservoirs i∈I and j∈I. The weighted average of these univariate distances ($\delta_{ij}^p$) is $d_{ij} \in R$: distance between individuals i∈I and j∈I. Each reservoir has neighboring reservoirs within a neighborhood threshold, $t_i \in R$: neighborhood threshold individual i∈I. Each reservoir either is (true or "1"), or is not (false or "0"), a nearest neighbor. A binary variable, $y_{ij} \in \{0,1\}$, indicates whether j∈I is one of K nearest neighbors to i∈I. So, treating each reservoir as a unitary set with the other reservoirs as a comparison set, the cross-validation pre-processor 122 identifies partitions 124, one partition for each reservoir.

The preferred automatic weighting unit 126 determines a property estimate value ($v_i$), preferably, using a k nearest-neighbor (k-NN) algorithm. Then, the automatic weighting unit 126 compares the known target property value ($f_i^\eta$) for each candidate set against that property estimate value to arrive at optimal weights. Preferably, the automatic weighting unit 126 uses an optimization model 1260 (e.g., any of various well known search techniques) to find mixed integer solution that minimizes the comparison difference, e.g., min $\Sigma_{i \in I}(v_i - \theta_i^\eta)^2$. Suitable well known such techniques include what are known as, for example, Branch and Bound, Branch and Cut, the Column Generation. Preferably, however, the automatic weighting unit 126 determines the optimal solution with application of a mixed integer quadratic programming (MIQP) model, such as CPLEX (www-01.ibm.com/software/integration/optimization/cplex-optimizer).

Inputs to the automatic weighting unit 126 include the known values of properties ($\theta_i^p$) of the reservoirs and known 2-norm univariate distances ($\delta_{ij}^p$) between the reservoirs. The automatic weighting unit 126 determines both $\theta_i^p$ and $\delta_{ij}^p$ from a monotonic transformation of the original input data, $\widehat{\theta_i^p}$. Thus, $$\theta_i^p = \frac{\widehat{\theta_i^p} - \min_{j \in I} \widehat{\theta_j^p}}{\max_{j \in I} \widehat{\theta_j^p} - \min_{j \in I} \widehat{\theta_j^p}}$$

and $\delta_{ij}^p = (\theta_i^p - \theta_j^p)^2$, $\forall p \delta P_\eta$, $\forall j \in I$. For a particular individual and a target property, subject to property estimate constraints 1262, neighboring distance constraints 1264-1268, weight constraints 1270, and neighboring member constraints 1272, the automatic weighting unit 126 optimizes over the weighted 2-norm distance function and, endogenously determines neighbors and target estimates.

Preferably, the automatic weighting unit 126 uses the optimization model 1260 as a global optimal similarity function, arrives at an optimum set of weights (w*) 128 that minimize forecasting error for each reservoir based on all other reservoirs. In this particular example, the difference between the known and predicted values of the target property indicates estimation error. The sum of squares of individual estimate errors indicates an overall estimation error. A perfectly predictable target value has zero error, i.e., that sum of squares is zero. Thus, iteratively selecting that that reduce overall estimation error until the error is minimized arrives at an optimum set of weights ($w_p \in [1,0]$: associated with property $p \in P$). Thus, the preferred automatic weighting unit 126 minimizes the overall error for each reservoir to arrive at optimum weights 128 and a unique similarity function applicable to all reservoirs. This set of optimal weights (w*) 128 and applicable similarity function may be applied to subsequently discovered, new reservoirs for automatically identifying analogous reservoirs.

Figure 3:
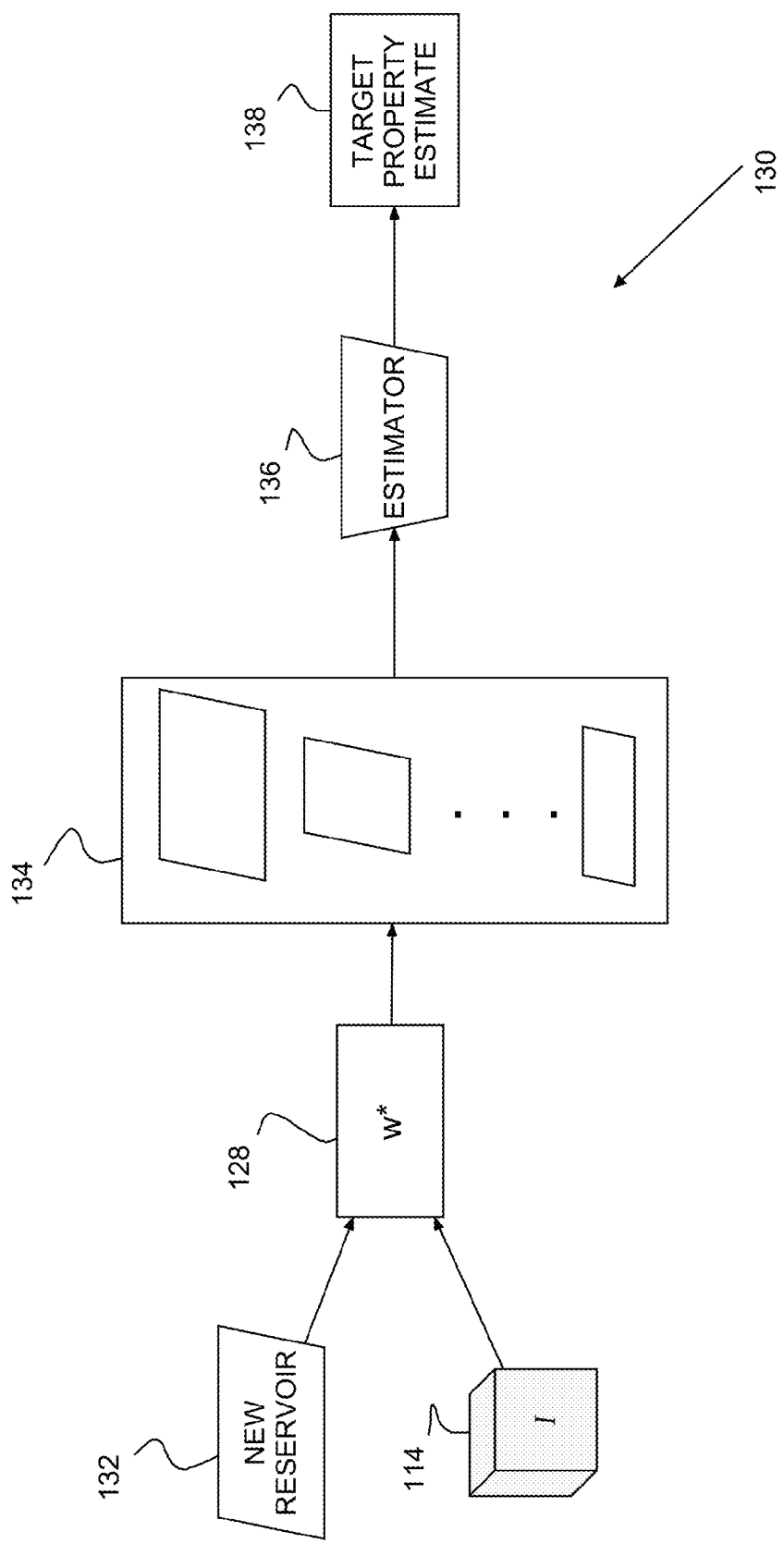
FIG. 3 shows an example of how a preferred system uses the determined set of optimal weights to weight neighboring reservoirs from the reservoir database and select analogous reservoirs for valuating new candidates.

FIG. 3 shows an example of how a preferred system (100 in FIG. 1) uses the automatically determined set of optimal weights (w*) 128 to weight neighboring reservoirs from the reservoir database (e.g., from storage 114) for valuating any new candidate(s) 132. The system 100 applies the optimal weights (w*) 128 in the similarity function to determine the similarity between the candidate reservoir and other listed reservoirs and automatically select 134 a subset analogous (i.e., most similar) reservoirs. So, for example, the subset may be a pre-defined number of reservoirs, or those listed reservoirs above a threshold value, e.g., in a weighted binary sum, may be selected. An estimator model 136, such as for example, a sample average estimator, a K-nn, or a linear regression, determines the previously unknown value 138 for the target reservoir 132 from the analogous reservoir subset 134.

Thus advantageously, the preferred system 100 automatically chooses properties, weights and an optimal similarity function for identifying analogous members of a population for new members, e.g., hydrocarbon reservoirs. Thus the preferred system and method guarantees formulating the best similarity function for estimating each particular target property based on existing available data and using a nearest-neighbor algorithm. Thus, a user, such as an expert, no longer manually makes these determinations and selections and results, e.g., analogous hydrocarbon reservoirs, are much less subjective.

While the invention has been described in terms of preferred embodiments, those skilled in the art will recognize that the invention can be practiced with modification within the spirit and scope of the appended claims. It is intended that all such variations and modifications fall within the scope of the appended claims. Examples and drawings are, accordingly, to be regarded as illustrative rather than restrictive.

What is claimed is:

1. A population comparison system comprising: a population storage storing a list of population members, each list entry including one or more characteristics for a respective population member and an analogous member list listing one or more other population members that have been previously identified as analogous to said respective population member;

an automatic weighting system automatically extracting weights (w*) for population member characteristics, said automatically extracted weights (w*) determining a similarity function for identifying analogous population members from said list, such that any error between the identified analogous members and said analogous member list is minimized, said automatic weighting unit comprising:

cross validation pre-processor partitions said population into a plurality of partitions, wherein said cross validation pre-processor partitions said plurality (I) into one partition for each member (i, where i∈I), each partition including two sub-groups, one sub-group including said each member (i) and the other sub-group including all other members remaining after excluding the respective said each member (Ii=I\{i}), and an objective model automatically selecting property weights to select from other said listed population members for each listed population member the same members as said more previously identified population members;

a new population member input receiving new population member descriptions including characteristics for each respective new population member;

an analogous member selector selecting a subset of listed population members as analogous members for each new population member responsive to said automatically extracted weights (w*) applied to said similarity function; and means for providing a value for said new population member estimated from the analogous members subset and using the estimated value to decide how to proceed with said new population member.

2. A population comparison system as in claim 1, wherein said population members are reservoirs (R) with properties (p∈P), each property has a known value ($\theta_i^P$), and said objective model compares said known value for a target property (η) against a property value estimate ($v_i \in R$: individual i∈I estimate of property η∈P) for said target property to arrive at property weights ($w_p \in [1,0]$).

3. A population comparison system as in claim 2, wherein said objective model minimizes the comparison difference and has the form:

$$\sum_{i \in I} (v_i - \theta_i^\eta)^2.$$

4. A population comparison system as in claim 2, wherein two reservoirs (i and j) are separated by a 2-norm univariate distance ($\delta_{ij}^P$), and inputs to said objective model include:

$\theta_i^P \in [1,0]$: (known) value of property p∈P of individual i∈I; and $\delta_{ij}^P \in [1,0]$: distance along property p∈P between reservoirs i∈I and j∈I.

5. A population comparison system as in claim 4, wherein reservoirs are separated by a distance, $d_{ij} \in R$: i∈I and j∈I;

each reservoir has K neighboring reservoirs within a neighborhood threshold, $t_i \in R$: i∈I; and said objective model optimizes subject to property estimate constraints, neighboring distance constraints, weight constraints, and neighboring member constraints.

6. A population comparison system as in claim 5, wherein property estimate constraints have the form $$v_i = \frac{1}{K} \sum_{j \in \Lambda\{i\}} \theta_j^\eta \cdot y_{ij},$$

where $y_{ij}$ indicates whether reservoir j is a nearest neighbor to reservoir i;
neighboring distance constraints have the form $d_{ij}=\Sigma_{p\in P_\eta}w_p \cdot \delta_{ij}^P$, $d_{ij} \leq t_i+(1-y_{ij})$ and $d_{ij} \geq t_i+y_{ij}$;
weight constraints have the form $\Sigma_{p\in P_\eta}w_p=1$; and
neighboring member constraints have the form $\Sigma_{p\in P_\eta}y_{ij}=K$;
where $\forall i \in I$ and $\forall j \in I$.

7. A population comparison system as in claim 1, said analogous member selector comprising:
a member selection unit applying said automatically extracted weights (w*) to new population member characteristics and automatically selecting listed members satisfying a threshold as members of said subset; and
an estimator determining said value for the new population member from said subset.

8. A population comparison system as in claim 7, wherein said threshold is a preselected number, said member selection unit selecting said preselected number of listed members with weighted properties closest to said the new population member.

9. A reservoir (R) valuation system comprising: a reservoir storage storing a reservoir database listing known reservoirs, each list entry including characteristics, and an analogous reservoir list listing one or more other reservoirs that are previously identified as analogous to the respective known reservoir;
an automatic weighting system automatically extracting weights (w*) for known reservoir characteristics, said automatically extracted weights (w*) determining a similarity function identifying analogous reservoirs from said list, such that any error between the identified analogous reservoirs and said analogous reservoir list is minimized;
a new reservoir input receiving new reservoir descriptions including characteristics for each respective said new reservoir;
an analogous reservoirs selection unit applying said automatically extracting weights (w*) in said similarity function to said new reservoir characteristics to automatically select a subset of known reservoirs satisfying a threshold; said automatic weighting unit comprises:
cross validation pre-processor partitions said population into a plurality of partitions, wherein said cross validation pre-processor partitions said plurality (I) into one partition for each member (i, where $i \in I$), each partition including two sub-groups, one sub-group including said each member (i) and the other sub-group including all other members remaining after excluding the respective said each member ($I_i=I\setminus\{i\}$), and
an objective model automatically selecting property weights to select from other said listed population members for each listed population member the same members as said more previously identified analogous reservoir;
an estimator determining a value for the said new reservoir from said subset; and one or more user terminals providing the estimated value, wherein the estimated value provides a decision of whether to pass or exploit said new reservoir.

10. A reservoir valuation system as in claim 9, wherein said reservoirs are hydrocarbon reservoirs with properties ($p \in P$), each property has a known value ($\theta_i^P$), and said objective model compares said known value for a target property ($\eta$) against a property value estimate ($v_i \in R$: individual $i \in I$ estimate of property $\eta \in P$) for said target property to arrive at property weights ($w_p \in [1,0]$).

11. A reservoir valuation system as in claim 10, wherein two reservoirs (i and j) are separated by a 2-norm univariate distance ($\delta_{ij}^P$), said objective model minimizes the comparison difference and has the form:

$$\min \sum_{i\in I} (v_i - \theta_i^\eta)^2;$$

and wherein, inputs to said objective model include:
$\theta_i^P \in [1,0]$: (known) value of property $p \in P$ of individual $i \in I$; and
$\delta_{ij}^P \in [1,0]$: distance along property $p \in P$ between reservoirs $i \in I$ and $j \in I$.

12. A reservoir valuation system as in claim 11, wherein
said hydrocarbon reservoirs are separated by a distance, $d_{ij} \in R$: $i \in I$ and $j \in I$;
each said hydrocarbon reservoir has K neighboring reservoirs within a neighborhood threshold, $t_i \in R: i \in I$; and
said objective model optimizes subject to property estimate constraints, neighboring distance constraints, weight constraints, and neighboring member constraints.

13. A reservoir valuation system as in claim 12, wherein said property estimate constraints have the form $$v_i = \frac{1}{K}\sum_{j\in I\setminus\{i\}} \theta_j^\eta \cdot y_{ij},$$

where $y_{ij}$ indicates whether reservoir j is a nearest neighbor to reservoir i;
neighboring distance constraints have the form $d_{ij}=\Sigma_{p\in P_\eta}w_p \cdot \delta_{ij}^P$, $d_{ij} \leq t_i+(1-y_{ij})$ and $d_{ij} \geq t_i+y_{ij}$;
weight constraints have the form $\Sigma_{p\in P_\eta}w_p=1$;
neighboring member constraints have the form $\Sigma_{p\in P_\eta}y_{ij}=K$;
where $\forall i \in I$ and $\forall j \in I$; and
said threshold is a preselected number, said member selection unit selecting said preselected number of known reservoirs with weighted properties closest to said the new reservoir.

14. A computer program product for comparing members of a population, said computer program product comprising a computer usable medium having computer readable program code stored thereon, said computer readable program code comprising:
computer readable program code means for storing a list of known population members, each list entry including one or more characteristics for a respective population member and an analogous member list listing one or more other population members that are previously identified as analogous to said respective population member, and further indicating each one or more previously identified analogous population members for each listed population member;
computer readable program code means for automatically extracting weights (w*) for population member characteristics, said automatically extracted weights (w*) determining a similarity function for identifying analogous population members from said list, such that any error between the identified analogous members and said analogous member list is minimized, said computer readable program code means for automatically extracting weights comprising:

computer readable program code means for partitioning said population (I) into a a plurality of partitions, one partition for each member (i, where i∈I), each partition including two sub-groups, one sub-group including said each member (i) and the other sub-group including all other members remaining after excluding the respective said each member (Ii=I\{i}), and computer readable program code means for automatically selecting property weights to select from other said listed population members for each listed population member the same members as said more previously identified population members;

computer readable program code means for receiving new population member descriptions including characteristics for each respective new population member; and computer readable program code means for selecting a subset of listed population members as analogous members for each new population member responsive to said automatically extracted determined weights (w*) applied to said similarity function, said subset being used to estimate a value for said new population member, the estimated value being used to decide how to proceed with said new population member.

15. A computer program product for comparing members of a population as in claim 14, wherein said population members are hydrocarbon reservoirs (R), computer readable program code means for receiving new population member descriptions comprises computer readable program code means for receiving description information directly from remotely connected sensors, automatically, or manually entered into one or more of the networked computers, and said computer readable program code means for automatically selecting comprises computer readable program code means for comparing a known value for a target property ($\eta$) against a property value estimate ($v_i \in R$: individual i∈I estimate of property $\eta \in P$) for said target property to arrive at property weights ($w_p \in [1,0]$).

16. A computer program product for comparing members of a population as in claim 15, wherein said computer readable program code means for automatically selecting further comprises computer readable program code means for minimizing the comparison difference and has the form:

$$\min \sum_{i \in I} (v_i - \theta_i^\eta)^2$$

for reservoirs separated by a distance, $d_{ij} \in R: i \in I$ and $j \in I$, where two reservoirs (i and j) are separated by a 2-norm univariate distance ($\delta_{ij}^P$), each reservoir has K neighboring reservoirs within a neighborhood threshold, $t_i \in R: i \in I$; and computer readable program code means for receiving inputs including:

$f_i^P \in [1,0]$: (known) value of property p∈P of individual i∈I, and $\delta_{ij}^P \in [1,0]$: distance along property p∈P between reservoirs i∈I and j∈I.

17. A computer program product for comparing members of a population as in claim 16, wherein computer readable program code means for automatically selecting optimizes subject to property estimate constraints, neighboring distance constraints, weight constraints, and neighboring member constraints, where property estimate constraints have the form $$v_i = \frac{1}{K} \sum_{j \in I \setminus \{i\}} \theta_j^\eta \cdot y_{ij},$$

where $y_{ij}$ indicates whether reservoir j is a nearest neighbor to reservoir i;

neighboring distance constraints have the form $d_{ij} = \sum_{p \in P_\eta} w_p \cdot \delta_{ij}^P$, $d_{ij} \le t_i + (1-y_{ij})$ and $d_{ij} \ge t_i + y_{ij}$;

weight constraints have the form $\sum_{p \in P_\eta} w_p = 1$; and neighboring member constraints have the form $\sum_{p \in P_\eta} = K$;

where ∀i∈I and ∀j∈I.

18. A computer program product for valuating reservoirs (R), said computer program product comprising a computer usable medium having computer readable program code stored thereon, said computer readable program code comprising:

computer readable program code means for storing a reservoir database with a list of a population of known reservoirs, each reservoir list entry including: characteristics for a respective known reservoir and an identification of one or more other listed said known reservoirs previously identified as analogous reservoirs;

computer readable program code means for partitioning said population (I) into a plurality of partitions, one partition for each member (i, where i∈I), each partition including two sub-groups, one sub-group including said each member (i) and the other sub-group including all other members remaining after excluding the respective said each member (Ii=I{i});

computer readable program code means for selecting property weights to select in each said partition analogous reservoirs from the second sub-group for the reservoir in the first group, such that the selected reservoirs are the same as the previously identified analogous reservoirs;

computer readable program code means for determining a set of weights (w*) for known reservoir characteristics and a similarity function independently identifying for said analogous reservoirs for said each known reservoir;

computer readable program code means for receiving new reservoir descriptions including characteristics for each respective new reservoir;

computer readable program code means for applying determined said weights (w*) to new reservoir characteristics and automatically selecting a subset of known reservoirs satisfying a threshold;

computer readable program code means for determining a value for said each respective new reservoir from said subset; and computer readable program code means for providing the determined value, wherein the determined value provides a decision of whether to pass or exploit said new reservoir.

19. A computer program product for comparing members of a population as in claim 18, wherein said population members are hydrocarbon reservoirs with properties (p∈P), each property has a known value ($\theta_i^P$), and said computer readable program code means for determining comprises:

computer readable program code means for comparing said known value for a target property ($\eta$) against a property value estimate ($v_i \in R$: individual i∈I estimate of property $\eta \in P$) for said target property to arrive at property weights ($w_p \in [1,0]$); and computer readable program code means for constraining said computer readable program code means for comparing, neighboring distance constraints, weight constraints, and neighboring member constraints, where whether reservoir j is a nearest neighbor to reservoir i is indicated by $y_{ij}$;

property estimate constraints have the form $$v_i = \frac{1}{K} \sum_{j \in N\{i\}} \theta_j^\eta \cdot y_{ij};$$

neighboring distance constraints have the form $d_{ij} = \Sigma_{p \in P_\eta} w_p \cdot \delta_{ij}^P$, $d_{ij} \leq t_i + (1-y_{ij})$ and $d_{ij} \geq t_i + y_{ij}$;

weight constraints have the form $\Sigma_{p \in P_{\eta,p}} = 1$; and neighboring member constraints have the form $\Sigma_{p \in P_\eta} y_{ij} = K$; where $\forall i \in I$ and $\forall j \in I$.

20. A computer program product for comparing members of a population as in claim 19, wherein said computer readable program code means for automatically selecting further comprises computer readable program code means for minimizing the comparison difference and has the form:

$$\min \sum_{i \in I} (v_i - \theta_i^\eta)^2$$

for reservoirs separated by a distance, $d_{ij} \in R$: $i \in I$ and $j \in I$, where two reservoirs (i and j) are separated by a 2-norm univariate distance ($\delta_{ij}^P$), each reservoir has K neighboring reservoirs within a neighborhood threshold, $t_i \in R$: $i \in I$; and computer readable program code means for receiving inputs including:

$\theta_i^P \in [1,0]$: (known) value of property $p \in P$ of individual $i \in I$, and $\delta_{ij}^P \in [1,0]$: distance along property $p \in P$ between reservoirs $i \in I$ and $j \in I$.

* * * * *